United States Patent [19]

Smith et al.

[11] Patent Number: 4,840,635
[45] Date of Patent: Jun. 20, 1989

[54] FULL-FASHION STUMP SHRINKER FOR THE RESIDUAL LIMB OF A HUMAN AMPUTEE

[75] Inventors: William B. Smith; Martha M. Field, both of Leawood, Kans.; Lawrence Pierce, Jr., Raytown, Mo.; Jeffrey C. Dalbey, Olathe, Kans.

[73] Assignee: Knit-Rite, Inc., Kansas City, Mo.

[21] Appl. No.: 894,651

[22] Filed: Aug. 8, 1986

[51] Int. Cl.⁴ ............................................. A61F 2/80
[52] U.S. Cl. ..................................................... 623/36
[58] Field of Search .................... 128/165, 82; 57/225, 57/224; 66/196; 623/36

[56] References Cited

U.S. PATENT DOCUMENTS

| | | | |
|---|---|---|---|
| 1,983,914 | 12/1934 | McCann | 128/165 |
| 3,451,232 | 6/1969 | Belzidsky | 623/36 |
| 3,460,338 | 8/1969 | Morrison | 57/225 |
| 3,985,003 | 10/1976 | Reed | 66/196 |
| 3,991,424 | 11/1976 | Prahl | 128/165 |

FOREIGN PATENT DOCUMENTS 2054380 2/1981 United Kingdom .................. 128/82

Primary Examiner—Richard J. Apley
Assistant Examiner—James Prizant
Attorney, Agent, or Firm—Hovey, Williams, Timmons & Collins

[57] ABSTRACT

The shrinker comprises a soft, pliable, sock-like receptacle for the stump having a closed toe and an open upper end. Initially flat, opposite sides of the shrinkere are joined along their longitudinal extremities without seams due to the one-piece, knitted construction of the shrinker. By knitting the shrinker on flatbed knitting machines, a tapered configuration without seams can be achieved through the technique of adding more knitting needles to progressively widen the shrinker as the knitting process is carried out after beginning at the toe. The lack of seams at the toe and along the sides increases comfort, and the yarn utilized for the knit fabric is stretchable to such an extent that at 50% stretch of the shrinker, a compression of approximately 10 to 30 millimeters of mercury is achieved, whereby to reduce edema and shape the stump in preparation for receiving a prosthesis.

8 Claims, 1 Drawing Sheet

U.S. Patent    Jun. 20, 1989    4,840,635
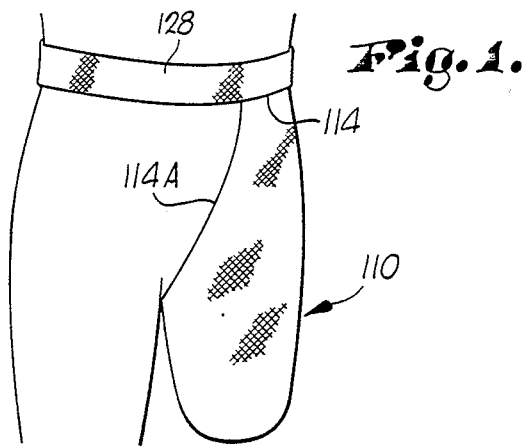
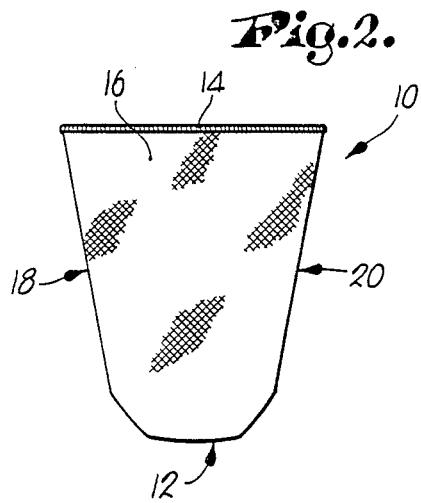
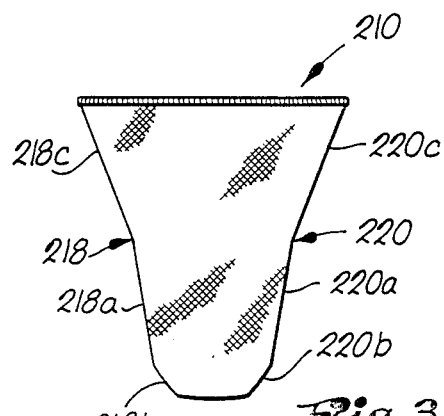
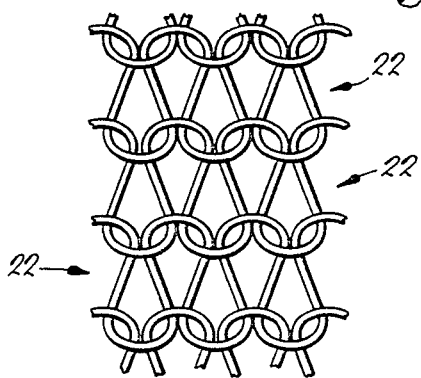
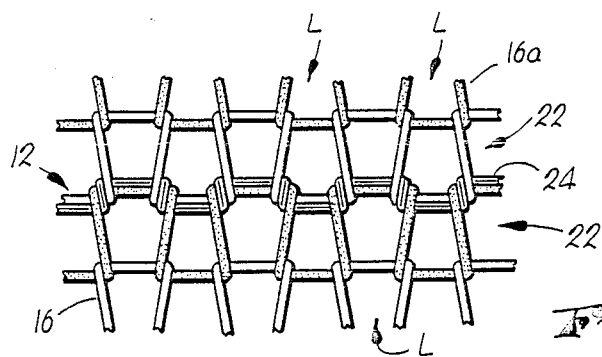
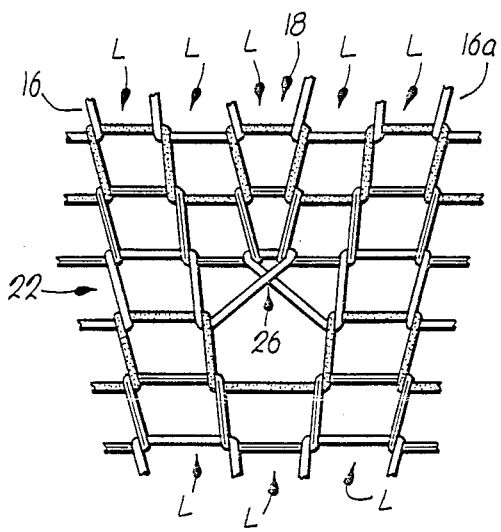

FULL-FASHION STUMP SHRINKER FOR THE RESIDUAL LIMB OF A HUMAN AMPUTEE

TECHNICAL FIELD

This invention relates to the field of prosthetics and, more particularly, to therapeutic, sock-like devices worn by an amputee immediately following amputation in order to prepare the residual limb for receiving a prosthesis.

BACKGROUND

The first few weeks following amputative surgery is a critical time for the amputee, both physically and emotionally. It is important during this period of time for the residual stump to be therapeutically compressed circumferentially so as to reduce the size and swelling of the stump from edema in preparation for fitting with a prosthesis.

It is also important, however, that the compressive force be carefully and properly applied in the sense that there must be greater pressure at the distal end of the stump than its upper or proximal end, since the opposite condition would have a tourniquet effect and prevent the vascular return of liquid upwardly through the stump toward the heart. Yet, the stump is also extremely sensitive at this time, and thus extreme care must be taken to avoid excessive compression or other irritation of the stump.

Accordingly, various types of stretchable, sock-like stump shrinkers have heretofore been provided in an effort to meet these needs. Such shrinkers have taken a variety of forms but have also presented a number of drawbacks.

For example, some shrinkers are simply constructed from two pieces of stretchable cloth material laid on top of one another and sewn together along their sides and across the toe so as to present a socket for the stump. However, this construction also produces distinct and bulky seams which can be quite irritating and uncomfortable to the patient, especially across the toe where the wound itself is located.

Others have been knitted on circular knitting machines so as to present a continuous, tubelike construction and thereby avoid the presence of longitudinal side seams. However, even in these shrinkers, the closure at the toe end is in the form of a separate circular pad or simply a sewn closed toe which must be sewn in place, or fabric (also called end cap), thereby presenting a rather thick, irritating seam at that location.

In some prior shrinkers the therapeutic compression is achieved by strands of elastic that encircle the shrinker. However, with that type of construction, the compression tends to vary dramatically depending upon the degree of stretch, since the elastic strands are simply being tensioned axially to greater and greater extents as the shrinker is stretched by insertion of the stump. In other words, depending upon the degree of stretch involved, the compressive snugness of the shrinker using the straight elastic strands will vary over a wide range, sometimes being too loose at the low end of the range where the stump is somewhat undersized and too high at the upper end of the range where the stump may be larger because of its shape. This can be a particular problem where the stump is irregularly shaped, since due to its irregularity, the stump may not cause the shrinker to be stretched to the point at which optimum therapeutic compression occurs, or, on the other hand, it may cause the shrinker to stretch so much at the point of irregularity that excessive compression occurs.

SUMMARY OF THE DESCRIPTION

Accordingly, one important object of the present invention is to provide a new and improved shrinker which not only provides improved therapeutic compression in the optimum manner, but is also considerably more comfortable for the patient than shrinkers previously available.

To this end, the shrinker of the present invention is constructed on a flatbed knitting machine so as to be of one piece, integral, knitted construction throughout, having a gradually outwardly tapering configuration beginning with the closed toe of the shrinker and terminating at the open opposite end thereof. The tapering effect is achieved by periodically adding additional knitting needles to the knitting process so that as the shrinker becomes longer and longer, it also becomes wider and wider through the addition of the extra needles. Thus, although there is a slightly discernable line of tiny irregularities or "fashionings" along the lateral extremities of the shrinker corresponding to the addition of each new needle, such line of irregularities is quite miniscule and is predominately on the outside of the shrinker so as to provide maximum comfort to the patient. Likewise, the closed toe of the shrinker comprises merely an extra run of yarn extending laterally across the shrinker formed by double-knitting the starting course of the shrinker, instead of a bulky seam or an additional, sewn on end cap. The yarn from which the shrinker is knitted has a stretchable core of spandex material wound helically with a soft rayon filament such that the shrinker exerts therapeutic compression in the range of approximately ten to thirty millimeters of mercury at fifty percent stretch of the knit fabric.

BRIEF DESCRIPTION OF THE DRAWING

FIG. 1 is a fragmentary, schematic front elevational view of a human amputee illustrating one form of the present invention utilized in connection with a waistband to support the shrinker where an above knee amputation is involved;

FIG. 2 is an elevational view of a second embodiment of the present invention for below knee amputees and illustrating essentially a single taper from adjacent the closed toe to the open upper end of the shrinker;

FIG. 3 is an elevational view of another embodiment of the invention for below knee amputees and constructed in the same manner as the shrinker of FIG. 2 but illustrating a double taper configuration;

FIG. 4 is an enlarged, fragmentary detail view of the stretchable yarn used in the shrinker of the present invention;

FIG. 5 is a greatly enlarged detail view of the interlaced loops of the knit fabric from which the shrinker of the present invention is constructed;

FIG. 6 is an enlarged detail view of the fabric construction at the closed toe of the shrinker looking at the toe in plan from below the shrinker as viewed in FIG. 2; and FIG. 7 is an enlarged, side-elevational detail view of an isolated portion along a lateral extremity of the shrinker illustrating a fashioning at which an additional knitting needle has been added to the series of needles preparing the shrinker.

DETAILED DESCRIPTION

Referring initially to FIG. 2, the shrinker 10 basically comprises a sock-like soft, pliable and elongated fabric receptacle having a closed lower end or toe 12 and an open upper end or mouth 14. The shrinker has a pair of initially flat, superimposed sidewalls 16 (only one being illustrated in FIG. 2, but see also FIGS. 6 and 7) joined to one another along their opposite, lateral extremities 18 and 20. As will hereinafter be explained in more detail, the shrinker is of one-piece construction with the sidewalls 16 being integrally joined together along extremities 18, 20, rather than being prepared from two separate pieces of material superimposed flatly against one another and then stitched along the side edges to present seams. The opposite sidewalls 16, by virtue of their interconnection along extremities 18, 20 and the closed toe 12, serve to define an interior socket which is initially flat but which then becomes rounded and full when a stump has been inserted thereinto as illustrated, for example, with the above knee model illustrated in FIG. 1.

The shrinker 10 is provided with a tapered configuration wherein the minimum transverse dimension is located across the toe 12 and the maximum transverse dimension is located at the upper end 14. This renders the shrinker 10 generally conical when its sidewalls 16 are distended, thus roughly approximating the tapering shape of the stump to be received within the shrinker 10. As noted in FIG. 2, the shrinker 10 may be sharply tapered just above the toe 12 and then more gradually tapered from that point on up to the upper end 14 so that the lower end of the shrinker 10 generally approximates a rounded configuration.

The shrinker 10 is of knitted fabric construction and its tapered configuration is obtained through full-fashion knit. That is, the shrinker 10 is prepared on a flatbed knitting machine and the tapered configuration is actually knitted into the shrinker itself by adding more needles to the line of needles across the width or the shrinker as the shrinker continues to grow longitudinally. This knit fabric construction is illustrated in FIG. 5 wherein it may be seen that the yarn strands are interlaced in connected loops generally denoted by the numeral 22.

. FIG. 6 illustrates the construction of the shrinker 10 at the toe 12 wherein the loops 22 are provided with a single extra crossrun 24 of yarn between the front and rear sidewalls 16 and 16a caused by double-knitting the first course of the shrinker at the commencement of the knitting process. In FIG. 6 the toe 12 is viewed in plan looking directly at the toe from the bottom of the shrinker so that portions of both the front and rear sidewalls 16 and 16a are illustrated, each vertical line L of the loops 22 as appearing in FIG. 6 representing one knitting needle on the flatbed machine.

FIG. 7 illustrates in more detail the manner in which full fashioning of the shrinker 10 causes the width of each sidewall 16 to increase as the upper end 14 of the shrinker is approached. In this respect, as additional knitting needles are placed in service at selected points in the longitudinal growth of the shrinker, a slight irregularity or "fashioning" is presented at each such point of needle addition. Thus, whereas in the lower part of FIG. 7 three lines L of the loops 22 are presented, five lines of loops L are presented at the upper part of that figure caused by the addition of two more needles, forming the slight irregularity which appears at the crossed connection in the center of the figure denoted broadly by the numeral 26. On the left of the crossed connection 26 is disposed the front sidewall 16 of the shrinker, while on the right of the connection 26 are those loops 22 associated with the rear sidewall 16a of the shrinker. It will be appreciated that the periodic crossed connections 26 appearing up the side extremities of the shrinker present a very faint but visible line on the exterior of the shrinker which, although discernable, causes no discomfort to the wearer.

The yarn in each loop of the knitted fabric is comprised of an elastic core 28 of spandex material wound helically with a soft rayon filament 30. As a result, the fabric exerts a relatively constant compressive load at fifty percent stretch. In this respect, depending upon the diameter of the yarn or the number of strands in each loop, the compressive load available from the shrinker may be varied. It has been found beneficial to have a heavy compression model which exerts a pressure of 25 to 30 milimeters of mercury at fifty percent stretch and a lighter compression model which exerts a pressure of 10 to 15 millimeters of mercury at fifty percent stretch. The heavier compression is best suited for reduction of edema and shaping of the stump, while the lighter compression is useful for tender stumps, nightime wear and stump size maintenance.

Preferably, the spandex core 28 of the yarn is 140 denier LYCRA brand spandex available from E. I. DuPont Nemours & Co., Inc., of Wilmington, Del. while the rayon filament 30 is 30/1 AVRIL brand rayon available from Avtex Fibers, Inc., of New York, N.Y. This results in a shrinker which is approximately 79% AVRIL brand rayon and 21% LYCRA brand spandex.

Due to the tapered configuration of the shrinker, the compressive load exerted by shrinker is greater distally, adjacent the toe end 12, than proximally adjacent the upper end 14. This is particularly important and critical to avoid a tourniquet effect and to encourage the excess liquid in the tissue cells to return upwardly toward the heart of the amputee when the shrinker is donned, as illustrated, for example in FIG. 1.

It will be noted in FIG. 1 that the shrinker 110 illustrated there is similar in construction to the shrinker 10 of FIG. 2, except that a waistbelt 128 is illustrated at the upper end 114 of the shrinker. Also, the upper end 114 includes a diagonal cut 114A leading downwardly to the groin area to provide additional comfort for the wearer.

In FIG. 3, the shrinker 210 is identical in construction to the shrinker of FIG. 2 except that a double taper is provided. In this respect, the medial area 218a and 220a of side extremities 218 and 220 taper at a lesser rate than the lower areas 218b and 220b, and likewise at a lower rate than the upper area 218c and 220c. Depending upon the shape of the amputee's stump, and the location of the amputation, any one of the embodiments of FIGS. 1, 2, or 3 may be preferable.

In view of the foregoing, it should be apparent that the present invention provides a significant improvement over conventional shrinkers. By eliminating the presence of protruding seams along the opposite sides and the toe of the shrinker, wearer comfort is significantly increased. Furthermore, the use of an elasticized material as the strands of the knit loops themselves produces a markedly more constant compressive hoading over a wider range of stretch than has heretofore been possible with shrinkers utilizing ere strands of plastic material running transversely of the fabric and not forming a part of the knit loops themselves. Still further, having the yarn material stretchable through its elasticized core and wound with soft rayon filament provides the desired stretch which accommodates irregularities and provides even compression over a wide stretch range, while also providing a soft comfortable and soothing finish to the shrinker which is especially important for the sensitive stump.

It will be apparent from the foregoing that minor changes could be made in the present invention by those skilled in the art without departing from the spirit of the present invention. Accordingly, the present invention should be limited only by a fair interpretation of the claims which follow.

I claim:

1. A stump shrinker for applying comfortable therapeutic compression of at least 10 to 30 millimeters of mercury at 50% stretch of the shrinker to the residual limb of a human amputee comprising:

an elongated, one-piece, soft, pliable fabric receptacle having a pair of flaccid sidewalls initially collapsed flatly against one another prior to donning of the shrinker by the amputee, said sidewalls being integrally interconnected along their opposite, longitudinal extremities so as to define an internal, stump-receiving socket which changes from a flattened condition before use to a condition conforming to the shape of the stump when the shrinker is worn by the amputee, said receptacle further having a normally open upper end through which the stump is inserted into the socket when the shrinker is donned by the amputee and a closed, seamless, normally lower toe disposed to engage and bear against the distal end of the stump when the shrinker is in place on the stump, said receptacle tapering toward a minimum transverse dimension as said toe is approached and being of full-fashion, knit construction whereby to provide said tapered configuration without seams along the longitudinal extremities of the sidewalls, said fabric being formed by resilient yarn of constant density throughout the shrinker and having such resilience that the shrinker exerts compression of at least 10 to 30 milimeters of mercury at 50% stretch of the fabric, said yarn being knitted in connected loops of substantially uniform pattern and number per square inch throughout the receptacle, whereby the shrinker exhibits generally uniform compression against the residual limb of the wearer over a wide range of stretch as the limb changes in diameter due to swelling and contraction.

2. A stump shrinker as claimed in claim 1, wherein said toe comprises an additional length of yarn extending transversely across the receptacle along the connection between loops from one sidewall and loops of the opposite sidewall formed by double-knitting a single course when knitting of the shrinker is commenced.

3. A stum shrinker as claimed in claim 2, wherein said yarn has a stretchable core wound helically about its exterior with a soft filament.

4. A stum shrinker as claimed in claim 3, wherein said core is spandex material and said filament is rayon material.

5. A stump shrinker as claimed in claim 1, wherein said toe comprises an additional strand of yarn extending transversely across the receptacle along the connection between loops from one sidewall and loops of the opposite sidewall formed by double-knitting a single course when knitting of the shrinker is commenced.

6. A stump shrinker as claimed in claim 5, wherein said yarn has a stretchable core wound helically about its exterior with a soft filament.

7. A stump shrinker as claimed in claim 1, wherein the rate of taper of the receptacle changes at predetermined locations along the extremity to the shape of the stump.

8. A stump shrinker as claimed in claim 1, wherein the receptacle is provided with a supporting belt at said upper end thereof for encircling the waste of the amputee.

* * * * *